(12) United States Patent
Finjan et al.

(10) Patent No.: US 9,370,471 B2
(45) Date of Patent: Jun. 21, 2016

(54) SLURRY POWDER COSMETIC COMPOSITIONS AND METHODS

(71) Applicants: Talal Finjan, Toronto (CA); Syed Rizvi, Brampton (CA); John R. Castro, Huntington Station, NY (US)

(72) Inventors: Talal Finjan, Toronto (CA); Syed Rizvi, Brampton (CA); John R. Castro, Huntington Station, NY (US)

(73) Assignee: ELC Management LLC, Melville, NY (US)

( * ) Notice: Subject to any disclaimer, the term of this patent is extended or adjusted under 35 U.S.C. 154(b) by 0 days.

(21) Appl. No.: 13/624,296

(22) Filed: Sep. 21, 2012

(65) Prior Publication Data

US 2014/0086964 A1    Mar. 27, 2014

(51) Int. Cl.
| | |
|---|---|
| A61K 8/02 | (2006.01) |
| A61Q 19/00 | (2006.01) |
| A61K 8/31 | (2006.01) |
| A61Q 1/02 | (2006.01) |
| A61K 8/58 | (2006.01) |
| A61K 8/891 | (2006.01) |
| A61K 8/895 | (2006.01) |

(52) U.S. Cl.
CPC ............... *A61K 8/022* (2013.01); *A61K 8/0241* (2013.01); *A61K 8/31* (2013.01); *A61K 8/585* (2013.01); *A61K 8/891* (2013.01); *A61K 8/895* (2013.01); *A61Q 1/02* (2013.01); *A61Q 19/00* (2013.01); *A61K 2800/594* (2013.01); *A61K 2800/624* (2013.01)

(58) Field of Classification Search
None
See application file for complete search history.

(56) References Cited

U.S. PATENT DOCUMENTS

| | | | |
|---|---|---|---|
| 3,439,088 | A | 4/1969 | Edman |
| 3,818,105 | A | 6/1974 | Coopersmith et al. |
| 4,804,538 | A | 2/1989 | Chen |
| 4,820,518 | A | 4/1989 | Murphy et al. |
| 4,967,810 | A | 11/1990 | Arashia |
| 4,970,252 | A | 11/1990 | Sakuta et al. |
| 5,236,986 | A | 8/1993 | Sakula |
| 5,412,004 | A | 5/1995 | Tachibana et al. |
| 5,496,544 | A | 3/1996 | Mellul et al. |
| 5,654,362 | A | 8/1997 | Schulz, Jr. et al. |
| 5,760,116 | A | 6/1998 | Kilgour et al. |
| 5,811,487 | A | 9/1998 | Schulz, Jr. et al. |
| 5,837,793 | A | 11/1998 | Harashima et al. |
| 6,303,105 | B1 | 10/2001 | Shah et al. |
| 6,964,773 | B1 | 11/2005 | Morrison |
| 6,991,782 | B2 | 1/2006 | Kanji et al. |
| 7,803,356 | B2 | 9/2010 | Lu et al. |
| 2001/0018432 | A1 | 8/2001 | Singleton et al. |
| 2003/0118530 | A1 | 6/2003 | O'Brien et al. |
| 2004/0105828 | A1 | 6/2004 | Chaiyawat et al. |
| 2004/0253284 | A1* | 12/2004 | Horino et al. ................ 424/401 |
| 2005/0100568 | A1* | 5/2005 | De Mul et al. .............. 424/401 |
| 2006/0034875 | A1 | 2/2006 | Nakanishi et al. |
| 2006/0155011 | A1 | 7/2006 | Frances et al. |
| 2008/0299059 | A1 | 12/2008 | Quadir |
| 2012/0039830 | A1 | 2/2012 | Kurahashi et al. |
| 2012/0039971 | A1 | 2/2012 | Kaneko et al. |

FOREIGN PATENT DOCUMENTS

| | | |
|---|---|---|
| EP | 2409684 | 1/2012 |
| JP | 61018708 | 1/1986 |
| JP | 07277924 | 10/1995 |
| JP | 2002-212030 | 7/2002 |
| JP | 2007-302800 | 11/2007 |
| JP | 2010-037216 | 7/2008 |
| JP | 2008214298 | 9/2008 |
| JP | 2009062324 | 3/2009 |
| JP | 2010037207 | 2/2010 |
| JP | 2010037207 A * | 2/2010 |
| JP | P2010-37207 | 2/2010 |
| JP | 2011-105605 | 6/2011 |
| JP | 2012-136495 | 7/2012 |
| JP | 2013-209317 | 10/2013 |
| WO | WO-2004/024798 | 3/2004 |

OTHER PUBLICATIONS

Translation of JP2010037207.*
PCT International Search Report; International Application No. PCT/CN2012/001720; Completion Date: Sep. 3, 2013; Date of Mailing: Sep. 26, 2013.
PCT Written Opinion of the International Searching Authority; International Application No. PCT/CN2012/001720; Completion Date: Sep. 17, 2013; Mailing Date: Sep. 26, 2013.
JP2010037207_Translation.
PCT International Search Report; International Application No. PCT/US2013/058382; Completion Date: Dec. 19, 2013; Mailing Date: Dec. 23, 2013.
PCT International Search Report; International Application No. PCT/US2013/058385; Completion Date: Dec. 19, 2013; Mailing Date: Dec. 23, 2013.
PCT Written Opinion of the International Searching Authority; International Application No. PCT/US2013/058382; Completion Date: Dec. 19, 2013; Mailing Date: Dec. 23, 2013.
PCT Written Opinion of the International Searching Authority; International Application No. PCT/US2013/058385; Completion Date: Dec. 19, 2013; Mailing Date: Dec. 23, 2013.
Supplemental European Search Report: EP13839440.8; Completion Date: Mar. 31, 2016; Mailing Date: Apr. 8, 2016.
Supplemental European Search Report; EP13839157; Completion Date: Mar. 31, 2016; Mailing Date: Apr. 11, 2016.

* cited by examiner

Primary Examiner — Mina Haghighatian
Assistant Examiner — Luke Karpinski
(74) Attorney, Agent, or Firm — Yonggang Wu

(57) ABSTRACT

Slurry powder cosmetic composition comprising particulates coated with a binder composition, a silicone gel composition, and the evaporation residue of an aqueous based composition and a method for making the composition.

24 Claims, No Drawingse

SLURRY POWDER COSMETIC COMPOSITIONS AND METHODS

TECHNICAL FIELD

The invention is in the field of cosmetic compositions in slurry powder form.

BACKGROUND OF THE INVENTION

Cosmetic compositions containing large amounts of powders, or particulate materials, are popular with consumers. Powders can be in compact or loose form and are used to apply color in the form of eyeshadow, blush, lip color, foundation, and so on. One of the difficulties in formulating such powders is due to their high concentration of particulate materials. Specifically in the powder manufacturing process, the particulate materials must be combined with a binder which is usually oils, waxes, or similar ingredients that cause the particulate materials to adhere to each other and to the skin. In many cases the particulate materials are unevenly coated with the binder composition. This results in powder particles that do not adhere well to the skin. In addition, the uneven coatings also cause the particulates to wear unevenly when applied to keratin surfaces. This means that sections of the applied powder will off preferentially leaving the user with an uneven look. Accordingly there is a need for developing powder processing methods and products where the particulates present can be evenly and thoroughly coated with the binder and/or other ingredients desires to provide treatment benefits.

In addition it is desirable to prepare powder compositions that may be used in their regular pressed or loose powder form, or alternatively may be diluted with water and other solvents to form color cosmetic compositions in semi-solid or liquid form.

It has been discovered that slurry powders coated with silicone gels and the evaporation residue of aqueous based compositions provide powders that adhere well to the skin, are readily hydratable, if desired. In addition, the aqueous based composition can be formulated to provide an evaporation residue that provides many treatment benefits.

SUMMARY OF THE INVENTION

The invention is directed to a slurry powder composition comprising particulate materials coated with at least one binder composition, at least one silicone gel composition and the evaporation residue of an aqueous based composition.

The invention is directed to a method for making a slurry powder composition comprising:
 (a) combining particulate materials with a binder composition, a silicone gel composition, and an aqueous based composition and slurrying the ingredients together;
 (b) evaporating off the aqueous based composition to yield particulate materials coated with the binder, the silicone gel composition and the evaporation residue of the aqueous based composition.

DETAILED DESCRIPTION

All percentages mentioned herein are percentages by weight unless otherwise indicated.

The term "evaporation residue" means a residue of ingredients that were solubilized or dispersed in the aqueous composition such as minerals, salts, ions, polymers, botanicals, etc. that will remain on the particulate materials after evaporation of aqueous based composition. Even if the aqueous based composition contains only water, the evaporation residue may contain minerals, salts, ions, or other ingredients.

The term "slurry powder" means a powder made by combining particulate materials with a binder composition, a silicone gel composition, and an aqueous based composition, mixing well, and then evaporating off the aqueous based composition to leave the particulate materials coated with the binder, the silicone gel composition and the evaporation residue.

The term "slurrying" means that the mixture of the particulate composition, the binder composition, and the silicone gel composition are combined with water and mixed well to coat the particulates.

In the final form the slurry powder compositions of the invention may be anhydrous. Alternatively the evaporation residue may comprise from about 0.1 to about 20% water such that the final slurry powder composition comprises from about 0.1 to 20% water.

I. The Particulates

The slurry powder cosmetic composition comprises particulates, either in the form of powders or pigments. Suggest ranges of particulates in the final composition range from about 0.1 to 99%, preferably from 0.5 to 95%, more preferably from about 1 to 90% by weight of the total composition. Preferred is where the particulates are from about 0.1 to 100 microns in diameter.

A. Powders

The particulates present may be colored or non-colored (for example white) non-pigmented powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

B. Pigments

Suitable particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

II. The Silicone Gel Composition

The slurry powder composition comprises at least one silicone gel composition. The silicone gel composition comprises at least one crosslinked organosiloxane elastomer and at least one nonpolar oil present in an amount sufficient to form a gel with the silicone elastomer. The gel may comprise from about 0.1 to 95%, preferably from about 1 to 80%, more preferably from about 5 to 75% of the nonpolar oil and from about 0.1 to 95%, preferably from about 1 to 80%, and more preferably from about 5 to 75% of the crosslinked organosiloxane elastomer.

A. The Silicone Elastomer

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in nonpolar oils as further set forth herein. Examples of silicone elastomer powders include vinyl dimethicone/methicone/silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluorosilicone elastomer, and hybrid silicone powders that contain a phenyl group such as Shin-Etsu's KSP-300, which is a phenyl substituted silicone elastomer; and Dow Coming's DC 9506. Examples of silicone elastomer powders dispersed in nonpolar oils include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crosspolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

Also suitable are silicone elastomers that have polar groups and which may be crosslinked; often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

B. The Nonpolar Oil

Suitable nonpolar oils include that may be used to form the silicone gel composition include, but are not limited to those set forth below:

1. Volatile Oils

Suitable volatile oils generally have a viscosity ranging from about 0.5 to 5 centistokes 25° C. and include linear silicones, cyclic silicones, paraffinic hydrocarbons, or mixtures thereof.

(a). Volatile Silicones

Cyclic silicones, generally referred to as cyclomethicones, are suitable including but not limited to those in cyclic form having 3, 4, 5, or 6 repeating Si-0 units.

Also suitable are linear volatile silicones, for example, those having the general formula:

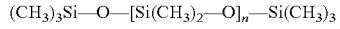

$(CH_3)_3Si-O-[Si(CH_3)_2-O]_n-Si(CH_3)_3$ where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated est)), octamethyltrisiloxane (1.0 est), decamethyltetrasiloxane (1.5 est), dodecamethylpentasiloxane (2 est) and mixtures thereof, with all viscosity measurements being at 25° C. Also suitable as the volatile silicone is methyl trimethicone, sold by Shin-Etsu Silicones under the trade name TMF 1.5, having a viscosity of 1.5 centistokes at 25° C.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Particularly suitable are volatile paraffinic hydrocarbons have a molecular weight of 70-225, preferably 160 to 190 and a boiling point range of 30 to 320, preferably 60 to 260° C., and a viscosity of less than about 10 est. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-Volatile Oils

A variety of nonvolatile oils are also suitable for use as the nonpolar oil. The nonvolatile oils generally have a viscosity of greater than about 5 to 10 centistokes at 25° C., and may range in viscosity up to about 1,000,000 centistokes at 25° C. Examples include, but are not limited to:

(a). Esters

Suitable esters are mono-, di-, and triesters. The composition may comprise one or more esters selected from the group, or mixtures thereof. Suitable monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Suitable triesters comprise the reaction product of a dicarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety, 3. Hydrocarbon Oils It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

4. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisoteate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

5. Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone. Also suitable are silicones having the CTFA names of dimethicone, phenyl dimethicone, diphenyl dimethicone, phenyl trimethicone, or trimethylsiloxyphenyl dimethicone. Other examples include alkyl dimethicones such as cetyl, cetearyl, stearyl, or behenyl dimethicone. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

III. The Binder

The slurry powder composition comprises a binder composition. The binder composition typically contains one or more lipophilic or amphiphilic ingredients that, when combined, act to bind the particulates together so that if and when they are pressed into a powder they will adhere to each other. The binder composition may comprise from about 1 to 95%, preferably from about 5-90%, more preferably from about 8-75% of the total slurry powder composition.

A. Nonpolar Oils

The binder composition may comprise one or more nonpolar oils as set forth above with respect to the silicone gel composition and in the same percentage ranges by weight of the total slurry powder composition.

B. Waxes

The binder composition may also contain solid or semisolid waxes that can provide structure. Suitable are animal, vegetable, mineral, or synthetic waxes. Suggested ranges are from about 0.1 to 50%, preferably from about 0.5 to 45%, more preferably from about 1-40% by weight of the total slurry powder composition. Preferred are waxes that have a melting point ranging from 30 to 110° C. Examples of such waxes include but are not limited to those made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

Also suitable are silicone waxes such as long chain alkyl silicone waxes, that is polydimethylsiloxanes having a substituted long chain alkyl (such as C14 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

C. Film Formers

The binder composition may also contain one or more oil soluble or dispersible film formers that are silicones, organic polymers or copolymers of silicone and organic monomers. Examples include but are not limited to:

1. Silicone Resins

Particularly suitable for use in the binder composition are one or more silicone resins having combinations of monofunctional (M), difunctional (D), trifunctional (T) and quadrifunctional (Q) units. The silicone resins may be partially or completely crosslinked. Examples of suitable silicone resins include trimethylsiloxy sillate, polymethylsilsesquixane, or derivatives thereof where the M, D, or T units may contain substitutions other than methyl, e.g. ethyl, propyl, butyl, or longer chain alkyl substituents such as C10-30 straight or branched chain alkyl groups.

2. Silicone Gums

Also suitable for use in the binder composition are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

IV. The Aqueous Based Composition

The aqueous based composition comprises water either alone or in combination with one or more additional ingredients. The aqueous based composition may be in the solution, suspension, or emulsion form. The aqueous based composition comprises from about 0.1 to 100%, preferably from about 0.5 to 95%, more preferably from about 1-80% water. In addition the aqueous based composition may comprise additional ingredients, including but not limited to those set forth below.

A. Polymers

The aqueous based composition may preferably contain one or polymers that may be film forming. If present such polymers may range from about 0.1 to 75%, preferably from about 0.5 to 65%, more preferably from about 1 to 60%. The film forming polymers may be water soluble or water dispersible. The slurry powder composition enables incorporation of significant amounts of water soluble or dispersible polymers that provide good end benefits. In the case of water soluble film forming polymers, they are not readily incorporated into traditional anhydrous based powder compositions. Examples of suitable polymers include but are not limited to those set forth herein.

Suitable polymers include those that may contain acrylate or acrylic acid and sulfonic acid repeat units. Examples of such polymers include those sold by Clariant under the Aristoflex trademark such as Aristoflex AVC (Ammonium acryloyldimethyltaurate/VP copolymer), Aristoflex HMB (Ammonium acryloyldimethyltaurate/beheneth-25 copolymer), Ammonium acryloyldimethyltaurate copolymer, and the like.

Also suitable are homopolymers, copolymers, and block and graft copolymers comprised of repeating monomers such as acrylic or methacrylic acid or esters thereof, urethanes, esters, amides, styrene, vinyl, silicon, and so on. Examples include acrylates copolymers sold under the trademark Covacryl such as Covacryl A15 or E14, or acrylates/ethylhexyl acrylate copolymer sold by Daito Kasei under the Daitosol 500SJ brand, or under the Dermacryl trademark (acrylates/octylacrylamide copolymer). Butyl acrylate/hydroxypropyldimethicone acrylate copolymers sold by Grant Industries, or acrylates/C12-22 alkylmethacrylate copolymers sold by Allianz, or sodium polystyrene sulfonates sold under Flexan trademark by Akzo Nobel.

Examples of such synthetic film forming polymers include those set forth in the CTFA Cosmetic Ingredient Dictionary and Handbook, Eighth Edition, 2000, pages 1744 through 1747.

Further examples of suitable polymers include copolymers of styrene and acrylic acid, methacrylic acid or their simple esters, including neutralized forms, for example styrene/acrylates/ammonium methacrylate copolymer, ammonium acrylates copolymer, acrylates/octylacrylamide copolymers, and so on.

Also suitable homo- or copolymers of PVP.

Also suitable are various synthetic polymers that may contain amide or amine substituent groups. Examples of such polymers include ammonium polyacrylate, acrylamides copolymer, acrylates/acrylamide copolymers, acrylates ammonium acrylate copolymer, acrylates $C_{10-20}$ alkyl acrylate cross polymer, acrylates/carbamate crosspolymer, acrylates ceteth-20 itaconate copolymer, acrylates/dimethylaminoethyl methacrylate copolymer, ammonium acrylates copolymer, ammonium polyacrylate, ammonium styrene/acrylates copolymer, ammonium vinyl acetate/acrylates copolymer, aminomethylpropanol/acrylates/dime-thylaminoethylmethacrylate copolymer, and so on.

A variety of natural polymers, or derivatives thereof may be suitable, including cellulosics, chitins, chitosans, shellac, rosins, resins, animal or vegetable proteins and polypeptides, and so on.

Examples of suitable cellulosic polymers include nitrocellulose, mono- or diesters of cellulose formed by the reaction of cellulose with various organic acids, for example straight or branched chain carboxylic acids having from one to twenty, preferably one to ten carbon atoms, which may be substituted with one or more hydroxyl groups, Examples of such cellulosics include cellulose acetate, cellulose acetate isobutyrate, cellulose acetate propionate, cellulose acetate propionate carboxylate. Also suitable are cellulose polymers prepared by reacting with groups such as hydroxyl, alkoxyalkyl, hydroxyalkyl where the alkoxyalkyl and alkyl groups have from about one to ten carbon atoms. Examples of such polymers are carboxylmethyl hydroxyethylcellulose, carboxymethylcellulose, ethyl cellulose, hydroxyethylcellulose, methyl ethylcellulose, hydroxypropylcellulose, hydroxylbutyl cellulose, hydroxybutyl methylcellulose, and so on.

Also suitable as polymers are various vegetable proteins including hydrolyzed animal protein, albumin, serum albumin, hydrolyzed wheat protein, hydrolyzed soy protein, hydrolyzed animal collagen, and mixtures thereof.

Also suitable are dextrans and alkoxy, or alkoxylalkyl derivatives thereof such as carboxymethyl dextran, carboxylethyl dextran, and so on.

B. Humectants

It may also be desirable to include one or more humectants in the aqueous based composition. If present, such humectants may range from about 0.001 to 25%, preferably from about 0.005 to 20%, more preferably from about 0.1 to 15%. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

C. Botanical Extracts

It may be desirable to include one or more botanical extracts in the aqueous based composition. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina Pavonica* extract, thermus thermophilis ferment extract, camelina saliva seed oil, boswellia serrata extract, olive extract, *Aribodopsis Thaliana* extract, *Acacia Dealbata* extract, *Acer Saccharinum* (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vitis Vinifera, Monts Nigra, Scutellaria Baicalensis, Anthemis Nobilis, Salvia Sclarea, Rosmarinus Officianalis, Citrus Medica Limonon, Panax Ginseng, Siegesbeckia Orientalis, Fructus Mwne, Ascophyllum Nodosum, Bifida Ferment lysate, Glycine Sofa extract, Beta Vulgaris, Haberlea Rhodopensis, Polygonum Cuspidatum, Citrus Aurantium Dulcis, Vitis Selaginella Tamar iscina, Huinulus Lupulus, Citrus Reticulata Peel, Punica Granatum, Asparagopsis, Curcuma Longa, Menyanthes Trifoliata, Helianthus Annus, Hordeum Vulgare, Cucumis Sativus, Evernia Prunastri, Evernia Furfuracea*, and mixtures thereof.

The composition may contain other ingredients such as preservatives, anti-oxidants, surfactants, non-foaming ingredients, and the like in any one or more of the phases.

The slurry powder composition of the invention may be used in its final form. In addition, it may be readily hydrated with water or nonpolar oils to form a semi-solid or liquid composition for application to skin.

The invention will be further described in connection with the following examples which are set forth for the purposes of illustration only.

Example 1

A slurry powder composition was prepared as follows:

Binder Composition:

| Seq | Ingredient | Wt % |
|---|---|---|
| 1 | Isododecane (nonpolar oil) | 10.00 |
| 1 | Hydrogenated polyisobutene (nonpolar oil) | 5.00 |
| 1 | Octyldodecyl stearoyl stearate (nonpolar oil) | 15.00 |
| 2 | Trimethylsiloxy silicate (film former) | 30.00 |
| 3 | Simethicone (anti-foam) | 0.50 |
| 4 | Microcrystalline wax (wax) | 5.00 |
| 5 | Polyglyceryl-2 triisostearate (nonpolar oil) | 14.50 |
| 6 | Dimethicone (nonpolar oil) | 15.00 |
| 6 | Dimethicone silylate/isododecane (40:60) (film former) | 5.00 |

The binder was prepared by combining the sequence 1 ingredients were combined in a glass beaker and heated to 80° C., mixing well with a propeller mixer. The sequence 2 ingredient was added to the mixture and mixed well, followed by addition of the sequence 3 ingredient. Mixing was continued for 4 minutes to ensure that no air bubbles were present. The sequence 4 ingredient was added with temperature maintained at 80° C. and mixing to ensure the wax was completely melted. The mixture was removed from the water bath and cooled to 50° C. while continuing the mixing. The sequence 5 ingredient was added, followed by sequence 6 ingredients, and mixed well. The composition was stored.

Particulate Composition+Binder Composition+Silicone Gel Composition:

| Seq | Ingredient | Wt % |
|---|---|---|
| 1 | Cloisonne Violet 525 (mica/titanium dioxide/carmine/ferric ferrocyanide) | 21.65 |
| 1 | Colorona Mica Black (iron oxides/mica/titanium dioxide) | 11.25 |
| 1 | Timica Nu Antique Silver (mica/titanium dioxide/iron oxides) | 5.60 |
| 1 | Ronastar (calcium aluminum borosilicate/silica/titanium dioxide) | 13.50 |
| 2 | Caprylyl glycol/phenoxyethanol/hexylene glycol | 0.50 |
| 3 | Binder Composition | 22.50 |
| 4 | Dimethicone/Polysilicone 11 (83:17) | 25.00 |

The particulate ingredients were combined in a glass beaker and mixed well. The binder composition was added with further mixing, followed by the silicone gel composition. Then 65 parts of this mixture was combined with 35 parts of water and mixed well to slurry the composition until the water has been absorbed by the particulates.

The slurry mixture is the placed in an aluminum pan and put into a Vetraco slurry machine. The machine parameters are set so that the left side press/vacuum setting is at 2.5 bars, vacuum time 6 seconds. The right side press/vacuum setting is at 5 bars with a vacuum time of 6 seconds. An ariana ribbon is placed on the top of the pan. After both cycles were completed the pan was removed from the machine and placed in a 45° C. oven for 60 minutes to evaporate the remaining water, if any.

Example 2

Comparative slurry powder cosmetic compositions were made as follows.

| Ingredient % by wt | 1 | 2 | 3 3923 | 4 3955A | 5 2335 | 6 4103 | 7 3947 | 8 | 9 3950A |
|---|---|---|---|---|---|---|---|---|---|
| Octyldodecyl stearoyl stearate (binder) | 4.50 | 4.5 | 4.50 | 3.38 | 3.45 | 4.50 | 4.50 | 3.75 | 3.375 |
| Polyglyceryl-2 Triisostearate (binder) | | | 4.35 | 3.26 | | | 4.35 | 3.63 | 3.26 |
| Preservatives (binder) | 0.50 | 0.50 | 0.50 | 0.50 | | 0.50 | 0.50 | 0.50 | 0.45 |
| Simethicone (binder) | | | 0.15 | 0.13 | | 0.50 | 0.50 | 0.13 | 0.12 |
| Microcrystalline Wax (binder) | 1.50 | 1.50 | 1.50 | 1.13 | 1.15 | 1.50 | 1.50 | 1.25 | 1.13 |
| Hydrogenated Polyisobutene (binder) | 1.50 | 1.50 | 1.50 | 1.13 | 1.15 | 1.50 | 1.50 | 1.25 | 1.13 |
| Dimethicone (binder) | 3.00 | 3.00 | 1.50 | 3.38 | 2.30 | 3.00 | 4.50 | 3.75 | 3.38 |
| Phenylpropyl-Dimethylsiloxy silicate (binder) | 7.50 | 7.50 | | | 5.75 | 7.35 | | | |
| Trimethyl-siloxy-Silicate (binder) | 9.00 | 9.00 | 9.00 | 6.75 | 6.90 | 9.00 | 9.00 | 7.50 | 6.75 |
| Dimethicone/Polysilicone 11[1] (Silicone gel) | | | | 10.00 | | | | | 10.00 |
| Dimethicone Silylate/isodo-Decane[2] (binder) | | | 1.50 | 1.13 | | | 1.50 | 1.25 | 1.13 |

-continued

| Ingredient % by wt | 1 | 2 | 3 3923 | 4 3955A | 5 2335 | 6 4103 | 7 3947 | 8 | 9 3950A |
|---|---|---|---|---|---|---|---|---|---|
| Isododecane (binder) | | | 3.00 | 2.25 | | 3.00 | 3.00 | 2.50 | 2.25 |
| C9-12 alkanes/ coco caprylate/ caprate (binder) | 3.00 | 3.00 | | | 2.30 | | | | |
| Colorona Mica Black[3] (Particulate) | 14.00 | 14.00 | 14.00 | 13.50 | 11.00 | 15.00 | 15.00 | | |
| Colorona Blackstar Red[4] (Particulate) | 27.90 | 27.90 | 27.90 | 26.00 | | | | | |
| Colorona Blackstar Gold[5] (Particulate) | 7.60 | 7.60 | 7.60 | 7.30 | | | | | |
| ASI sericite GMS 4C[6] (Particulate) | 20.00 | 20.00 | 20.00 | 20.20 | | | | 5.00 | 4.50 |
| Cloisonne Violet (Particulate)[7] | | | | | 11.00 | 29.00 | 29.00 | | |
| Timicu Nu Antique Silver[8] (Particulate) | | | | | | 7.50 | 7.50 | | |
| Ronastar Noble Sparks[9] (Particulate) | | | | | 14.50 | 18.00 | 18.00 | | |
| Ronastar Purple Sparks[10] (Particulate) | | | | | 14.50 | | | | |
| Cloisonne Blue[11] (Particulate) | | | | | | | | 5.00 | 4.50 |
| Talc (Particulate) | | | | | | | | 1.25 | 1.13 |
| Ultramarine Blue (Particulate) | | | | | | | | 5.00 | 4.50 |
| Colorona Bronze[12] (Particulate) | | | | | | | | 58.25 | 52.43 |
| Mirage Glamour Gold[13] (Particulate) | | | | | 26.00 | | | | |

[1] Gransil DM5: 83 parts dimethicone/17 parts Polysilicone 11
[2] Dow Corning 7-4405 Cosmetic Fluid: 60 parts isododecane/40 parts dimethicone silylate
[3] Iron oxides/mica/titanium dioxide
[4] Iron oxides/mica
[5] Iron oxides/mica
[6] mica/isopropyl titanium triisostearate/sodium lauroyl aspartate/zinc chloride
[7] mica/titanium dioxide/ferric ferrocyanide
[8] mica/titanium dioxide/iron oxides
[9] calcium aluminum borosilicate/silica/titanium dioxide/tin oxide
[10] calcium aluminum borosilicate/titanium dioxide/silica
[11] mica/titanium dioxide/ferric ferrocyanide
[12] mica/iron oxides
[13] calcium sodium borosilicate/titanium dioxide/tin oxide The compositions were prepared by combining the binder ingredients as set forth in Example 1. The particulates were added. For Formulas 4 and 9 the gel composition was also added. Then 65 pails of this mixture was combined with 35 parts of aqueous based composition comprising water. The slurried mixture was placed into aluminum pans and treated in a Vetraco slurry machine and dried as set forth in Example 1.

Example 3

Compositions 1-9 above were compared by trained evaluators who applied the compositions by picking up application portion with a sponge applicator and applying to the same portion of their forearm with 4 strokes. The effects were visually assessed and are set forth below:

| Formula No. | Evaluation |
|---|---|
| 1 | Intense payoff of background color, very minimal shine |
| 2 | High shine but poor intensity of background color, poor wear |
| 3 | Low shine, low color intensity |
| 4 | High shine, high background color intensity, superior wear |

-continued

| Formula No. | Evaluation |
|---|---|
| 5 | High shine, minimal background color intensity, major dusting |
| 6 | High color intensity, minimal shine |
| 7 | High shine, high color intensity |
| 8 | Intense color, minimal shine, and uneven application |
| 9 | High shine, color intensity, brighter. Smoother application |

The slurry powder composition of the invention provided superior shin, color intensity, and wear.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

The invention claimed is:

1. A slurry powder cosmetic formulation in the form of an evaporation residue of a slurry mixture comprising:
   particulates coated with a pre-mixed binder composition that contains at least one nonpolar oil selected from the group consisting of dimethicone, $C_{2-30}$ fatty acid esters, paraffinic hydrocarbons and mixtures thereof; at least one synthetic wax having a melting point of from about 30° C. to about 110° C., and at least one film former selected from the group consisting of trimethylsiloxy silicate, dimethicone silylate and mixtures thereof prior to incorporation into the slurry mixture;
   a silicone gel composition comprising an organosiloxane elastomer solvated in dimethicone; and
   an aqueous based composition comprising water;
   wherein the binder composition comprises 5 to 75% by weight of said final slurry powder cosmetic formulation.

2. The formulation of claim 1 wherein the particulates comprise pigments or non-pigmented particulates.

3. The formulation of claim 2 wherein the pigments or non-pigmented particulates have a particle size of from about 0.01 to 100 microns.

4. The formulation of claim 3 wherein the pigments or non-pigmented particulates are surface treated prior to coating with the pre-mixed binder composition.

5. The formulation of claim 1 wherein the silicone gel composition comprises a mixture of dimethicone and a crosslinked organosiloxane elastomer.

6. The formulation of claim 1 wherein the silicone gel composition comprises a mixture of dimethicone and Polysilicone-11.

7. The formulation of claim 1 wherein the aqueous based composition comprises water and an ingredient selected from the group consisting of water soluble or water dispersible film forming polymers, humectants, botanical extracts and mixtures thereof.

8. The formulation of claim 7 wherein the aqueous based composition comprises water and at least one water soluble or dispersible film forming polymer.

9. The formulation of claim 7 wherein the aqueous based composition comprises water and at least one humectant.

10. The formulation of claim 7 wherein the evaporation residue of the slurry mixture is solvatable with non-polar solvents.

11. The formulation of claim 1 wherein the particulates have a particle size ranging from about 0.01 to 100 microns; the silicone gel composition comprises a mixture of dimethicone and Polysilicone-11; and wherein the aqueous based composition comprises an ingredient selected from the group consisting of water soluble polymer, humectant, botanical extract, and mixtures thereof.

12. The formulation of claim 1 which is anhydrous.

13. The formulation of claim 1 comprising from about 0.1 to 20% water.

14. The formulation of claim 1 wherein the paraffinic hydrocarbon is isododecane, polyisobutene, hydrogenated polyisobutene, or mixtures thereof.

15. The formulation of claim 1 wherein the ester comprises a glyceryl ester.

16. The formulation of claim 14 wherein the silicone gel composition comprises a mixture of dimethicone and Polysilicone-11.

17. A slurry powder cosmetic formulation comprising the evaporation residue of the slurrying mixture comprising iron oxides or titanium dioxides coated, prior to incorporation into the formulation, with a binder composition that contains (a) at least one nonpolar oil selected from the group consisting of dimethicone, C2-30 fatty acid esters, paraffinic hydrocarbons, and mixtures thereof, (b) at least one synthetic wax having a melting point from 30-110° C., and (c) at least one film former selected from the group consisting of trimethylsiloxy silicate and dimethicone silylate; a silicone gel composition comprising an organosiloxane elastomer solvated in dimethicone; and an aqueous based composition, where the iron oxides or titanium dioxides present in the formulation are evenly and thoroughly coated with the binder composition and the silicone gel composition.

18. The formulation of claim 7 wherein the aqueous based composition comprises water and at least one botanical extract.

19. The formulation of claim 8 wherein the aqueous based composition comprises from about 0.1 to 75% of water soluble or water dispersible film forming polymers.

20. The formulation of claim 9 wherein the aqueous based composition comprises from about 0.001 to 25% humectants.

21. The formulation of claim 18 wherein the aqueous based composition comprises from about 0.0001 to 10% botanical extracts by weight of the total formulation.

22. A method for making a slurry powder formulation comprising the steps of:
   (a) combining at least one nonpolar oil selected from the group consisting of dimethicone, $C_{2-30}$ fatty acid esters, paraffinic hydrocarbons and mixtures thereof; at least one synthetic wax having a melting point of from about 30° C. to about 110° C., and at least one film former selected from the group consisting of trimethylsiloxy silicate, dimethicone silylate and mixtures thereof to form a binder composition;
   (b) coating particulates with the binder composition of (a),
   (c) adding a silicone gel composition comprising dimethicone and a silicone elastomer to the mixture of (b)
   (d) adding an aqueous based composition comprising an ingredient selected from the group consisting of water soluble or water dispersible film forming polymers, humectants, botanical extracts and mixtures thereof to the mixture of (c),
   (e) subjecting the mixture of (b), (c), and (d) to slurrying;
   (f) evaporating the aqueous based composition from the slurry mixture,
   to yield a slurry powder formulation which is the evaporation residue of the slurry mixture and contains 5 to 75% by weight of the total formulation of the binder composition.

23. The method of claim 22 wherein the slurrying is performed until the aqueous based composition has been absorbed by the particulates.

24. The method of claim 22 wherein the slurry powder formulation contains from about 0.01 to 20% water.

* * * * *